(12) United States Patent
Hagiwara et al.

(10) Patent No.: US 9,494,611 B2
(45) Date of Patent: Nov. 15, 2016

(54) IMMUNOLOGICAL ANALYZING APPARATUS

(71) Applicant: HITACHI HIGH-TECHNOLOGIES CORPORATION, Tokyo (JP)

(72) Inventors: Takaaki Hagiwara, Hitachinaka (JP); Yoshiyuki Tanaka, Hitachinaka (JP); Kazunori Yamazawa, Mito (JP)

(73) Assignee: Hitachi High-Technologies Corporation, Tokyo (JP)

(*) Notice: Subject to any disclaimer, the term of this patent is extended or adjusted under 35 U.S.C. 154(b) by 2 days.

(21) Appl. No.: 14/678,168

(22) Filed: Apr. 3, 2015

(65) Prior Publication Data

US 2015/0212102 A1 Jul. 30, 2015

Related U.S. Application Data

(63) Continuation of application No. 13/513,884, filed as application No. PCT/JP2010/072891 on Dec. 20, 2010, now abandoned.

(30) Foreign Application Priority Data

Dec. 21, 2009 (JP) .................................. 2009-288622

(51) Int. Cl.
*G01N 35/00* (2006.01)
*G01N 35/10* (2006.01)

(52) U.S. Cl.
CPC .. *G01N 35/00722* (2013.01); *G01N 35/00584* (2013.01); *G01N 35/1004* (2013.01); *G01N 35/1009* (2013.01); *G01N 2035/00891* (2013.01); *G01N 2035/1013* (2013.01); *Y10T 436/11* (2015.01)

(58) Field of Classification Search
None
See application file for complete search history.

(56) References Cited

U.S. PATENT DOCUMENTS 7,384,601 B2 6/2008 Matsubara et al.

FOREIGN PATENT DOCUMENTS

| EP | 359049 A2 | 3/1990 | |
| EP | 0359049 A2 * | 3/1990 | ....... G01N 35/00712 |
| JP | 01-288768 A | 11/1989 | |
| JP | 02-080962 A | 3/1990 | |

(Continued)

OTHER PUBLICATIONS

Japanese Office Action received in corresponding Japanese Application No. 2011-547537 dated Jan. 6, 2015.

(Continued)

*Primary Examiner* — Jyoti Nagpaul
*Assistant Examiner* — Julie Tavares
(74) *Attorney, Agent, or Firm* — Mattingly & Malur, PC

(57) ABSTRACT

An automatic analyzer comprises selection means for selecting whether a preparatory operation, specified from a plurality of analysis preparation processes of the automatic analyzer, should be executed in an initial process at the powering on of the analyzer or after the start of the actual analysis (i.e., in parallel with the sample analysis operation). For example, the automatic analyzer is equipped with means which allows the analyzer to execute a "system liquid replacement operation", a "sample nozzle pressure sensor checking operation", a "reaction vessel discarding operation" and a "pre-cleaning liquid replacement operation" which among various operations that are executed in the preparation process in conventional immunological analyzing apparatus in processes other than the preparation process.

6 Claims, 13 Drawing Sheets

(56) References Cited

FOREIGN PATENT DOCUMENTS

| | | |
|---|---|---|
| JP | 03-051760 A | 3/1991 |
| JP | 04-295763 A | 10/1992 |
| JP | 05-264555 A | 10/1993 |
| JP | 08-285661 A | 11/1996 |
| JP | 10-232234 A | 9/1998 |
| JP | 11-023581 A | 1/1999 |
| JP | 2002-162400 A | 6/2002 |
| JP | 2005-241612 A | 9/2005 |
| JP | 2007-183152 A | 7/2007 |
| JP | 2009-162733 A | 7/2009 |
| JP | 2009-270940 A | 11/2009 |

OTHER PUBLICATIONS

Japanese Office Action received in Japanese Application No. 2011-547537 dated May 20, 2014.

* cited by examiner

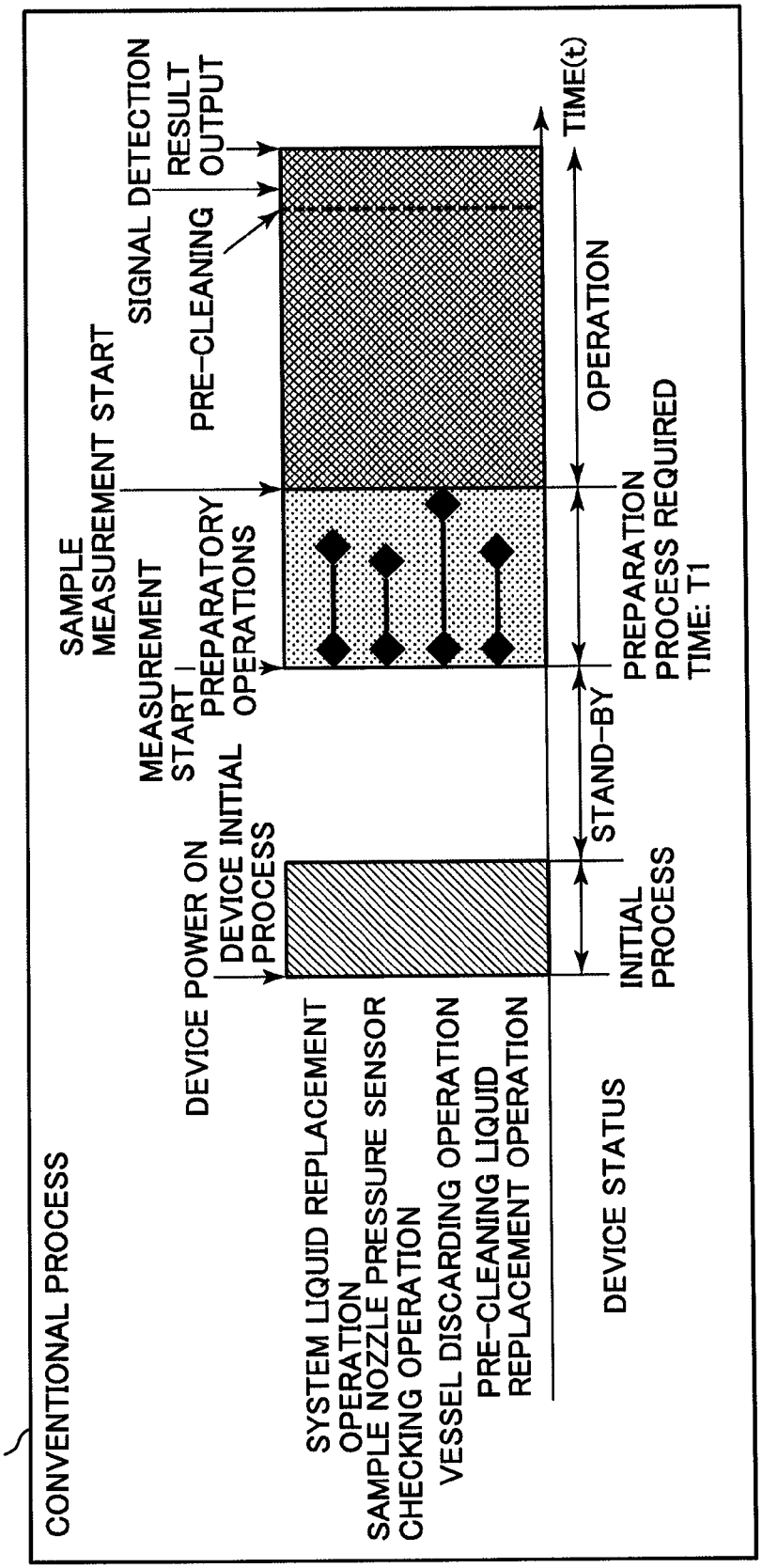

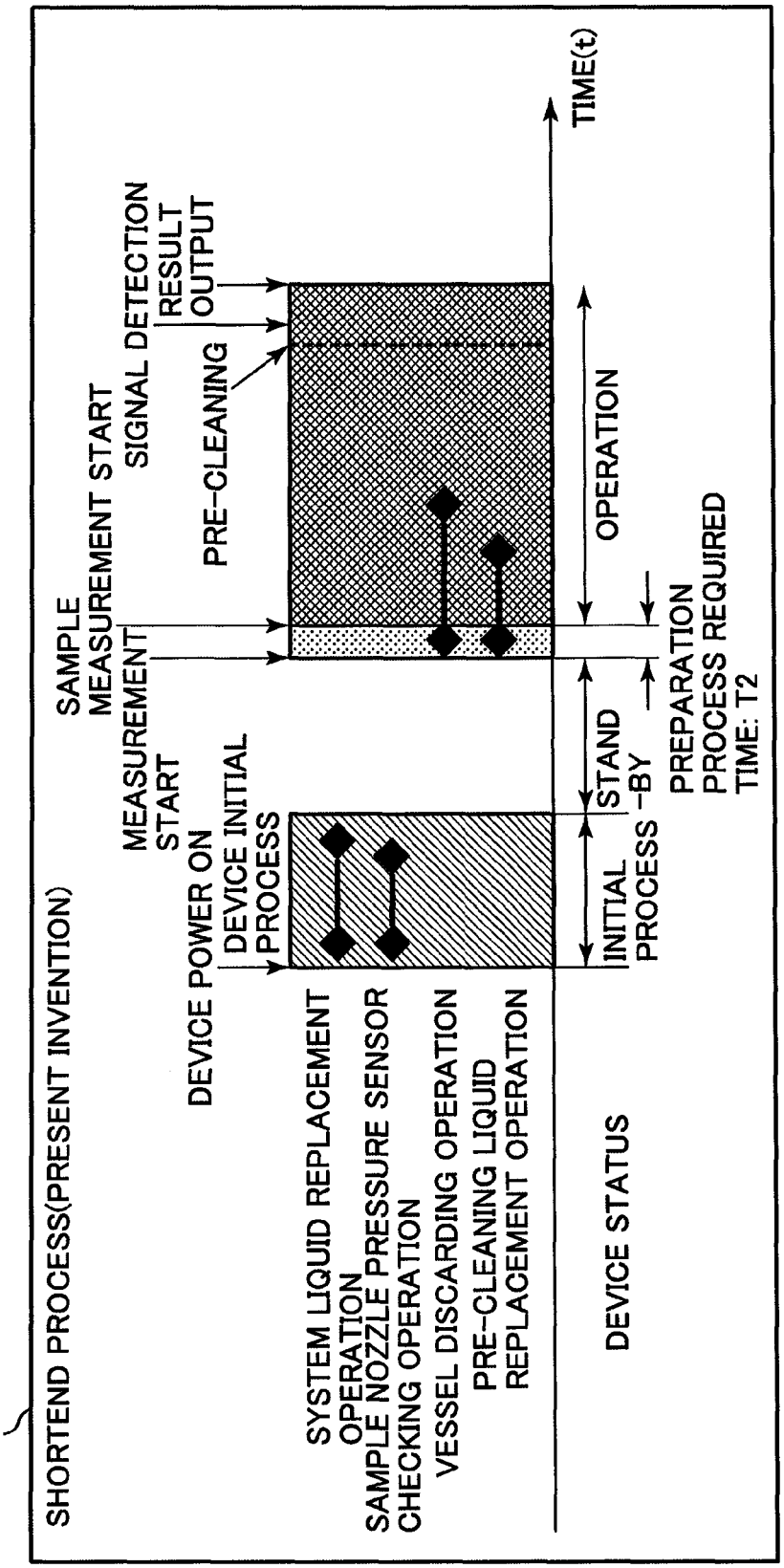

FIG. 10A

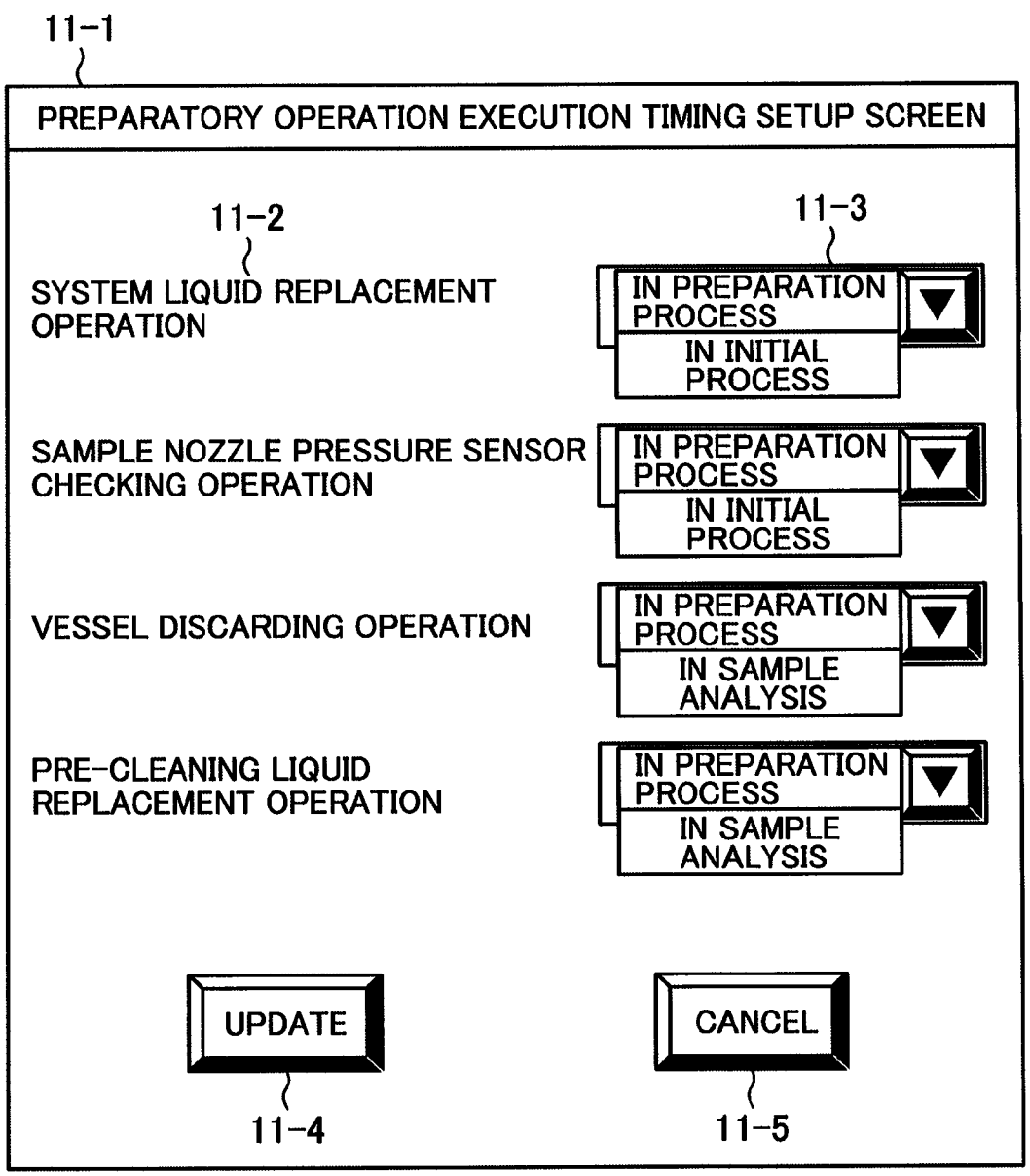

IMMUNOLOGICAL ANALYZING APPARATUS

TECHNICAL FIELD

The present invention relates to an automatic analyzer for analyzing biological samples such as blood and urine, and in particular, to an automatic analyzer having a function of automatically executing an analysis preparation process before the start of the analysis.

BACKGROUND ART

Automatic analyzers for automatically conducting qualitative/quantitative analyses of constituents of biological samples (blood, urine, etc.) are roughly classified into biochemical automatic analyzers and immunological analyzing apparatus. Such an automatic analyzer is generally set in an operable state in which mechanisms/equipment and reagents necessary for the measurement are usable by conducting the following two processes after the user's powering on of the apparatus (analyzer) and before the start of the actual sample measurement:

(1) Initial Process after the Power of the Apparatus is Turned on and Before the Apparatus Shifts to the Standby State The initial process is executed only once after the power is turned on, and thus is not executed thereafter as long as the apparatus is energized continuously. The initial process may include, for example, a cleaning process for cleaning reaction vessels used for the measurement.

(2) Analysis Preparation Process after a Measurement Start Request is Received and Before the Measurement of a Sample is Started The analysis preparation process is executed each time the operator instructs the apparatus to start the measurement, and thus is executed once or multiple times per day depending on the operational conditions of the inspection room. The analysis preparation process may include, for example, a system liquid replacement operation for replacing system liquid to be circulated in the flow cell together with the reaction solution.

Patent Document 1 is known to have disclosed a technique for increasing the efficiency of the former one of the above two processes (i.e., (1) initial process after the powering on of the apparatus). The technique makes it possible to increase the efficiency of the initial process in a manner suiting the operational conditions of the facility, by allowing the user to edit the contents and the order of steps of the initial process, equipping the apparatus with means for previously executing a process before the operator arrives at the facility (e.g., automation using a timer), etc. On the other hand, there has been proposed no technique for shortening or increasing the efficiency of the analysis preparation process which is executed after the reception of the measurement start request and before the start of the sample measurement.

PRIOR ART LITERATURE

Patent Document

Patent Document 1: JP-2-80962-A

SUMMARY OF THE INVENTION

Problem to be Solved by the Invention

The problem described after is common to all automatic analyzers while the following explanation will be given by taking an immunological analyzing apparatus as an example. When the power is turned on, an immunological analyzing apparatus of the standard type shifts to the standby state after executing an initial operation at the startup. The standby state is a state in which the apparatus can receive the analysis start request from the user. Upon receiving the analysis start request, the apparatus executes the in-apparatus preparation process and thereafter shifts to the actual sample analysis.

Immunological analyzing apparatus generally take a long time for the aforementioned preparation process, that is, preparatory operations to be done after the reception of the analysis start request but before the actual start of sample measurement by the apparatus. The preparatory operations may include, for example, a "system liquid replacement operation", a "sample nozzle clog checking operation", a "reaction vessel discarding operation", a "pre-cleaning liquid replacement operation", etc. The system liquid replacement operation is an operation for previously replacing the system liquid inside a channel with fresh system liquid in order to supply the fresh system liquid to a detecting device in the apparatus. The sample nozzle clog checking operation is an operation for checking whether there is a clog in the sample suction nozzle. The reaction vessel discarding operation is an operation for discarding a reaction vessel remaining in the apparatus when the reaction vessel supposed to have already been discarded still remains in the apparatus due to abnormal interruption of the previous operation before normal termination. The pre-cleaning liquid replacement operation is an operation for previously replacing the pre-cleaning liquid inside a channel with fresh pre-cleaning liquid in order to supply the fresh pre-cleaning liquid to a pre-cleaning device which cleans the reaction product before the detection.

Taking these preparatory operations into account, it generally takes approximately 15 minutes from the pressing of the start button to the sampling of the first sample. Once the preparatory operations are finished and the analyzer shifts to the continuous operation state, the turnaround time between the inspection request and the outputting of the result substantially equals the reaction time. However, for a sample for which the inspection request is made first in a day or for which the measurement is conducted immediately after a restart of the analyzer after shifting to the standby state due to absence of inspection request for a certain time period, the measurement is started after executing the preparatory operations. Thus, the actual turnaround time of such a sample till the acquisition of the result becomes approximately 15 minutes longer than that in the case of continuous analysis. Therefore, shortening the time of the analysis preparation process and acquiring the result within a short turnaround time as close as possible to that in continuous analysis even in inspection immediately after the start are common needs of clinical laboratories.

To meet the above needs, it is possible to previously execute the analysis preparation process in the initial process immediately after the startup of the apparatus. However, simply employing such a method can lead to problems with the precision of the analysis data acquired by the analysis. For example, suppose the "system liquid replacement operation" is executed in the initial process immediately after the startup of the apparatus, the system liquid can deteriorate during the standby state when the measurement is not started quickly after the shift to the standby state after the startup (i.e., when the standby state is long) due to the user's operational conditions, even though there is no problem when the measurement is started quickly after the shift to the standby state. Conducting analysis using deteriorated system liquid can adversely affect the precision of the analysis data.

It is therefore the primary object of the present invention to provide an automatic analyzer having means for shortening the turnaround time of inspection just after the startup of the apparatus by optimizing the operations in the analysis preparation process without deteriorating the precision of the analysis data.

Means for Solving the Problems

In order to achieve the above object, an automatic analyzer in accordance with the present invention comprises selection means for selecting whether a preparatory operation, specified from a plurality of analysis preparation processes of the automatic analyzer, should be executed in an initial process at the powering on of the analyzer or after the start of actual analysis (i.e., in parallel with the sample analysis operation). The analysis preparation processes may include, for example, a "system liquid replacement operation", a "sample nozzle pressure sensor checking operation", a "reaction vessel discarding operation", a "pre-cleaning liquid replacement operation", etc. The selection on whether the preparatory operation should be executed in the initial process or after the start of the analysis is made possible for at least the above four operations. For example, the automatic analyzer may be equipped with means capable of previously setting the analyzer to execute the system liquid replacement operation and the sample nozzle pressure sensor checking operation in the initial process at the powering on of the analyzer and to execute the reaction vessel discarding operation and the pre-cleaning liquid replacement operation after the start of the actual analysis (i.e., in parallel with the sample analysis operation). With the setting, the time necessary for the preparation process is shortened.

By providing the automatic analyzer with a user interface which lets the user set the timing of execution of each preparatory operation through a screen, etc., the user is allowed to select whether each preparatory operation should be executed in the preparation process as in the conventional techniques, in the initial process after the powering on of the analyzer, or in the sample analysis, and determine operational conditions suitable for each inspection facility.

However, the following problems can occur when the system liquid replacement operation is executed in the initial process after the powering on of the analyzer according to the means described after.

For example, when the time period from the end of the initial process after the powering on of the analyzer to the start of the measurement (i.e., the standby state) is long, the system liquid can deteriorate during the standby state. Further, since the standby state is a state in which the apparatus maintenance operation can be conducted, the system liquid inside the channel is replaced with water when a particular maintenance operation such as water replacement is performed. In such cases, the system liquid necessary for sample measurement has become invalid at the point of the sample measurement.

To resolve this problem, the automatic analyzer may be equipped with means which automatically judges whether the system liquid is currently valid or invalid and notifies the user of the result of the judgment. Specifically, the time of execution of the system liquid replacement operation is stored in a storage device in the automatic analyzer and the elapsed time till the present is determined from the stored time and the present time. The system liquid is judged to be valid if the elapsed time is within a preset permissible time period, or invalid if the elapsed time has exceeded the permissible time period. When a maintenance operation like water replacement is performed by the user during the standby, a history record of the execution of the maintenance operation is stored in the storage device of the automatic analyzer. The system liquid is judged to be invalid if no system liquid replacement operation has been performed since the maintenance operation. In cases where the automatic analyzer is instructed to start the measurement when the system liquid is still in the invalid state, the automatic analyzer enables itself to start the sample measurement by automatically executing the system liquid replacement operation in the preparation process as in the conventional techniques. It is also possible to change the system liquid from invalid state to the valid state by equipping the automatic analyzer with means for letting the user conduct the system liquid replacement operation when the system liquid is in the invalid state.

Effects of the Invention

According to the present invention, the time of the preparation process necessary before the immunological analyzing apparatus actually dispenses the sample can be shortened compared to that in conventional techniques.

In conventional immunological analyzing apparatus, for example, it generally takes approximately 15 minutes from the pressing of the start button to the sampling of the first sample when the preparation process is taken into account. The present invention makes it possible to execute the "system liquid replacement operation", the "sample nozzle pressure sensor checking operation", the "reaction vessel discarding operation" and the "pre-cleaning liquid replacement operation" among the preparatory operations which are executed in the preparation process in the conventional techniques with different timing, by which the time from the pressing of the start button to the sampling of the first sample can be shortened to several minutes. Therefore, the turnaround time for samples for which the inspection request is made first in a day or for which the measurement is conducted immediately after a restart of the analyzer after shifting to the standby state due to absence of inspection request for a certain time period can be shortened significantly compared to that in the conventional techniques. Consequently, improvement of operational efficiency of the entire inspection facility can be expected. Further, thanks to the means for validating the system liquid even when the system liquid has become invalid before the start of the measurement due to the operational conditions, effects such as improvement of operational efficiency of inspection and saving of consumable articles can be expected without deteriorating the precision of the analysis.

BRIEF DESCRIPTION OF THE DRAWINGS

FIG. 5A is a schematic diagram showing an example of a process flow from the powering on of the apparatus to the outputting of the result in a conventional technique.

FIG. 5B is a schematic diagram showing reduction of the turnaround time of inspection just after the start, which is achieved by shortening the required time of the preparation process by employing the present invention.

FIG. 10A is a schematic diagram showing an example of a screen displayed for notifying the user whether the system liquid is valid or invalid.

FIG. 11 is a schematic diagram showing an example of an operation screen for setting the timing of execution of each preparatory operation.

MODE FOR CARRYING OUT THE INVENTION

Figure 1A:
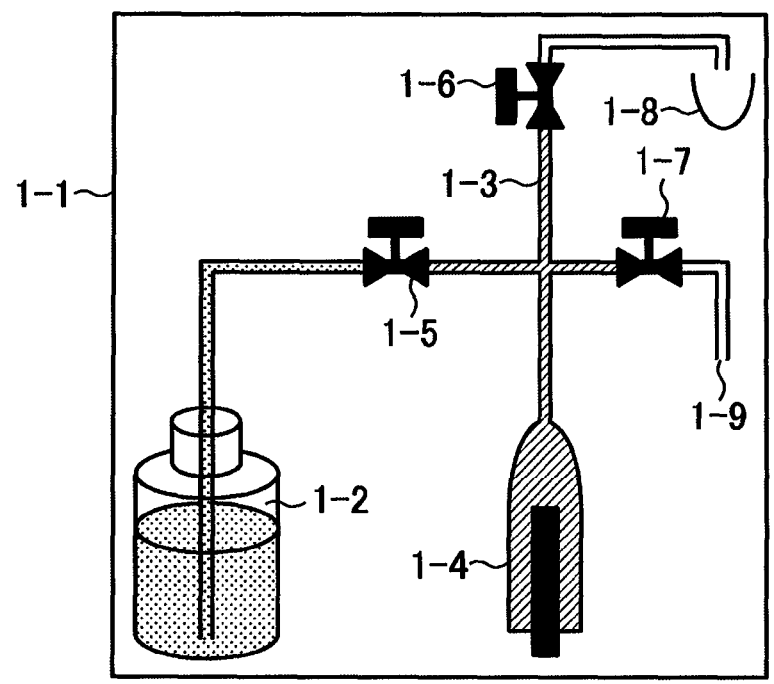
FIG. 1A is a schematic diagram showing a state of a system liquid channel and a system liquid replacement action before the execution of a system liquid replacement operation in an immunological analyzing apparatus in accordance with an embodiment of the present invention.

Referring now to the drawings, a description will be given in detail of a preferred embodiment in accordance with the present invention.

First, a "system liquid replacement operation", a "sample nozzle pressure sensor checking operation", a "reaction vessel discarding operation" and a "pre-cleaning liquid replacement operation", as preparatory operations which should be conducted by an immunological analyzing apparatus before the actual sample analysis, will be explained referring to figures.

Figure 1B:
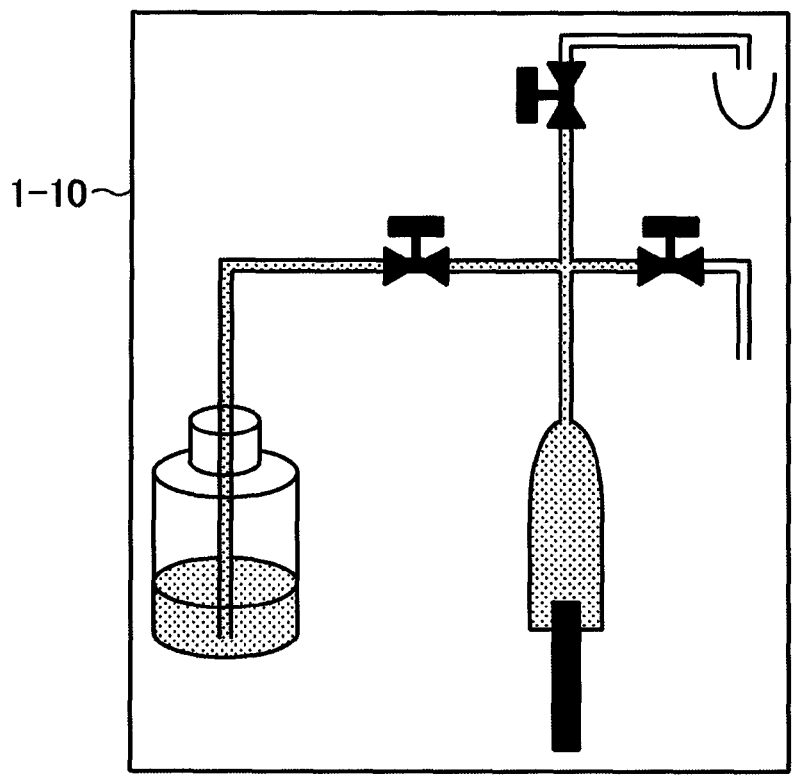
FIG. 1B is a schematic diagram showing a state of the system liquid channel and a system liquid replacement action after replaced with fresh system liquid in the immunological analyzing apparatus in accordance with an embodiment of the present invention.

First, an example of the system liquid replacement operation will be explained referring to FIGS. 1A and 1B. FIG. 1A shows an example of a channel for the supply of the system liquid in the immunological analyzing apparatus. The reference numeral 1-1 represents a state before the execution of the system liquid replacement operation. The reference numeral 1-2 represents a system liquid bottle and 1-3 represents the channel for the system liquid filled with old system liquid in FIG. 1A. The reference numeral 1-4 represents a syringe, 1-5 represents a first valve, 1-6 represents a second valve, 1-7 represents a third valve, and 1-8 represents a reservoir which is separately arranged in the apparatus for supplying the system liquid to a detecting device. The reference numeral 1-9 represents a drain hole for pouring unnecessary liquid into the drain. At the start of the system liquid replacement operation, the second valve 1-6 is opened and the syringe 1-4 is pulled. Subsequently, the second valve 1-6 is closed, the third valve 1-7 is opened, and the syringe 1-4 is pushed, by which the old system liquid is poured into the drain through the drain hole 1-9. Subsequently, the third valve 1-7 is closed, the first valve 1-5 is opened, and the syringe 1-4 is pulled so as to suck new system liquid from the system liquid bottle 1-2 and fill the channel with the new system liquid. FIG. 1B (1-10) shows the state in which the old system liquid in the channel has been replaced with the fresh system liquid by the above operation.

Figure 2:
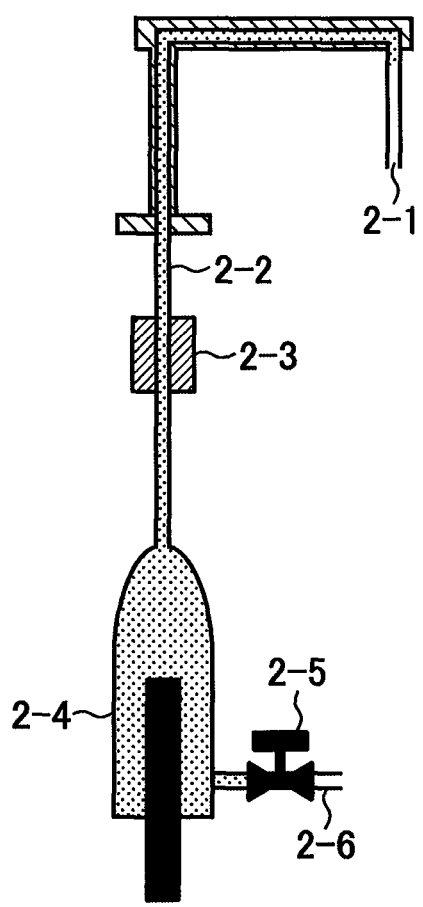
FIG. 2 is a schematic diagram showing an example of a sample nozzle of the immunological analyzing apparatus and a sample nozzle pressure sensor checking operation in accordance with an embodiment of the present invention.

Next, an example of the sample nozzle pressure sensor checking operation will be explained referring to FIG. 2. FIG. 2 shows an example of a nozzle mechanism of the immunological analyzing apparatus for sucking in the sample. The reference numeral 2-1 represents a sample suction hole, 2-2 represents a channel, 2-3 represents a pressure sensor for checking whether there is a clog in the channel or not, 2-4 represents a syringe, 2-5 represents a valve, and 2-6 represents an internal washing water supply hole. At the start of the sample nozzle pressure sensor checking operation, the valve 2-5 is opened, by which internal washing water is supplied to the inside of the channel through the internal washing water supply hole 2-6. Subsequently, the valve 2-5 is closed and the syringe 2-4 is pulled, by which air is sucked in through the sample suction hole 2-1. Whether the pressure sensor 2-3 is operating with no problem or not is checked by measuring the pressure in the channel with the pressure sensor 2-3 along with the suction of air.

Figure 3:
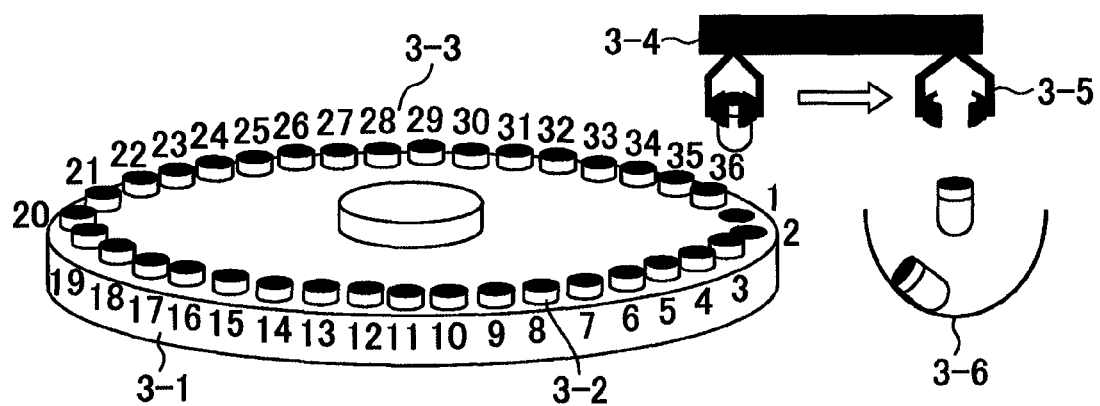
FIG. 3 is a schematic diagram showing an example of a reaction vessel setting mechanism of the immunological analyzing apparatus and a reaction vessel discarding operation in accordance with an embodiment of the present invention.

Next, an example of the reaction vessel discarding operation will be explained referring to FIG. 3. In FIG. 3, the reference numeral 3-1 represents a reaction vessel setting mechanism of the rotary type, 3-2 represents disposable reaction vessels, 3-3 represents position numbers marked on the reaction vessel setting mechanism, 3-4 represents a reaction vessel transfer mechanism, 3-5 represents a holding mechanism of the reaction vessel transfer mechanism, and 3-6 represents a waste bag for used reaction vessels. In the reaction vessel discarding operation, reaction vessel setting positions setting spots are successively moved to the position of the reaction vessel transfer mechanism 3-4 by stepwise rotation of the reaction vessel setting mechanism 3-1. The reaction vessel transfer mechanism detects whether there is a reaction vessel remaining at the position or not by closing and opening the holding mechanism 3-5. If a reaction vessel remains at the position, the reaction vessel transfer mechanism holds the reaction vessel with the holding mechanism, transfers the reaction vessel horizontally to the waste bag 3-6 for the used reaction vessels, and discards the reaction vessel into the waste bag. The above operation is repeated for all the reaction vessel setting positions, by which all the positions on the rotary reaction vessel setting mechanism 3-1 are set in the vacant state before the analysis.

Figure 4A:
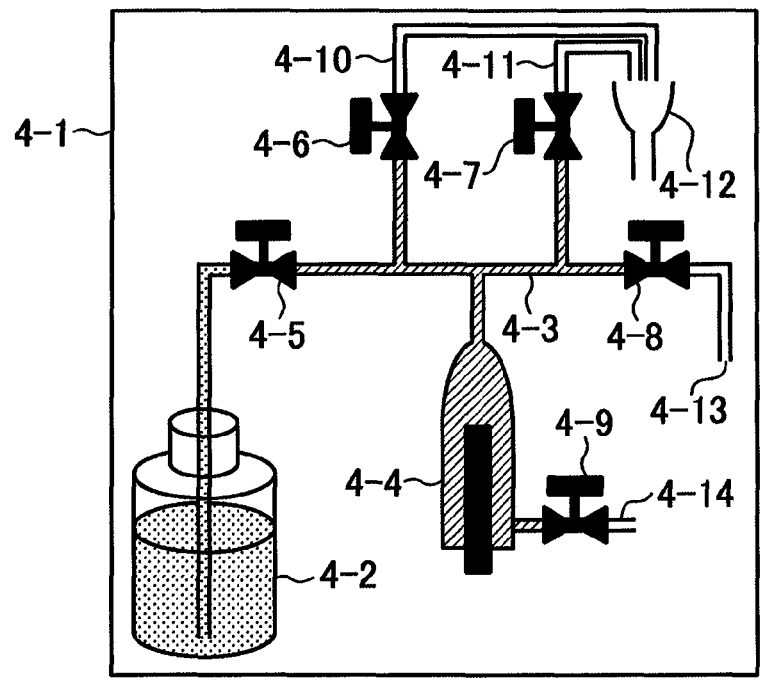
FIG. 4A is a schematic diagram showing a state of a pre-cleaning liquid channel and a pre-cleaning liquid replacement action before the execution of a pre-cleaning liquid replacement operation in the immunological analyzing apparatus in accordance with an embodiment of the present invention.
Figure 4B:
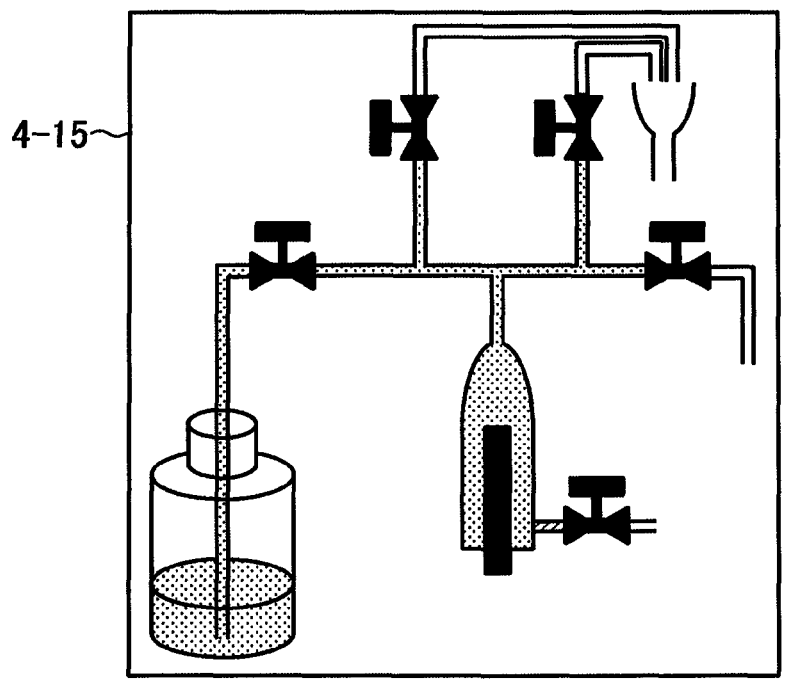
FIG. 4B is a schematic diagram showing a state of the pre-cleaning liquid channel and a pre-cleaning liquid replacement action after replaced with fresh pre-cleaning liquid in the immunological analyzing apparatus in accordance with an embodiment of the present invention.

Next, an example of the pre-cleaning liquid replacement operation will be explained referring to FIGS. 4A and 4B. FIG. 4A shows an example of a channel for the supply of pre-cleaning liquid in the immunological analyzing apparatus. The reference numeral 4-1 represents a state before the execution of the pre-cleaning liquid replacement operation. The reference numeral 4-2 represents a pre-cleaning liquid bottle and 4-3 represents the channel for the pre-cleaning liquid filled with old pre-cleaning liquid in FIG. 4A. The reference numeral 4-4 represents a syringe, 4-5 represents a first valve, 4-6 represents a second valve, 4-7 represents a third valve, 4-8 represents a fourth valve, 4-9 represents a fifth valve, 4-10 represents a discharging nozzle, and 4-11 represents a suction nozzle. The reference numeral 4-12 represents a reservoir which is separately arranged for supplying the pre-cleaning liquid to a pre-cleaning device, 4-13 represents a drain hole for pouring unnecessary liquid into the drain, and 4-14 represents an internal washing water supply hole. At the start of the pre-cleaning liquid replacement operation, the third valve 4-7 and the fifth valve 4-9 are opened and the internal washing water is supplied through the internal washing water supply hole 4-14 and discharged into the reservoir 4-12, by which the suction nozzle 4-11 is washed and cleaned up. Subsequently, the pre-cleaning liquid is sucked in from the pre-cleaning liquid bottle 4-2 by closing the third valve 4-7 and the fifth valve 4-9, opening the first valve 4-5 and pulling the syringe 4-4. Subsequently, surplus liquid is poured into the drain through the drain hole 4-13 by closing the first valve 4-5, opening the fourth valve 4-8 and pushing the syringe 4-4. Subsequently, the fifth valve 4-9 is opened, by which the internal washing water is supplied through the internal washing water supply hole 4-14 and poured into the drain through the drain hole 4-13. Subsequently, the pre-cleaning liquid is sucked in from the pre-cleaning liquid bottle 4-2 by closing the fourth valve 4-8 and the fifth valve 4-9, opening the first valve 4-5 and pulling the syringe 4-4. Subsequently, the pre-cleaning liquid is supplied to the inside of the discharge nozzle by closing the first valve 4-5, opening the second valve 4-6 and pushing the syringe 4-4. Subsequently, surplus liquid is poured into the drain through the drain hole 4-13 by closing the second valve 4-6, opening the fourth valve 4-8 and pushing the syringe 4-4. Subsequently, the syringe 4-4 is filled with the internal washing water by supplying the internal washing water through the internal washing water supply hole 4-14 by opening the fifth valve 4-9. Finally, the fourth valve 4-8 and the fifth valve 4-9 are closed. FIG. 4B (4-15) shows the state in which the old pre-cleaning liquid in the channel has been replaced with the fresh pre-cleaning liquid by the above operation.

Means for executing the above preparatory operations "system liquid replacement operation", "sample nozzle pressure sensor checking operation", "reaction vessel discarding operation", "pre-cleaning liquid replacement operation" with different timing in a process other than the conventional preparation process will be described below referring to FIGS. 5A and 5B.

FIG. 5A (5-1) shows a conventional technique. When the power of the apparatus is turned on by the operator, the apparatus shifts to an initial process state and executes an initial process necessary for the operation of the apparatus. After finishing the initial process, the apparatus shifts to a standby state. In this state, the operator can start the measurement with arbitrary timing by, for example, pressing a start button of the apparatus. At the start of the measurement in response to the operator's instruction, the apparatus shifts to a preparation process state. In this state, the apparatus carries out the preparatory operations which have to be conducted before the measurement of actual samples "system liquid replacement operation", "sample nozzle pressure sensor checking operation", "reaction vessel discarding operation", "pre-cleaning liquid replacement operation", etc. in parallel. After finishing all these operations, the apparatus shifts to an operation state. In the operation state, the apparatus starts the measurement of the actual sample. A reaction is caused by mixing the sample with a reagent. After the reaction finished, the apparatus conducts the pre-cleaning which is cleaning the reaction product before the detection, thereafter determines the quantities of constituents in question by detecting signals from the reaction product with a detector, and outputs the result of the measurement. In regard to the first measurement after the start, the time necessary for acquiring the result since the measurement start instruction by the operator that is turnaround time equals the sum of the actual reaction time and the required time t1 of the preparation process.

In contrast, the turnaround time of each subsequent sample for which the inspection request is made after the apparatus has shifted to the operation state is substantially equal to the actual reaction time since the preparatory operations are conducted only once after the start of the measurement.

Next, an example of reduction of the turnaround time of the first measurement after the start, achieved by shortening the required time t1 of the preparation process according to the present invention, will be explained referring to FIG. 5B (5-2). Among the four preparatory operations explained above, the "system liquid replacement operation" and the "sample nozzle pressure sensor checking operation" are executed not in the preparation process state but in the initial process state since these operations do not necessarily have to be executed at every start of measurement as long as the operations are completed before the actual sample measurement. By this method, the required time of the preparation process after the start of the measurement can be shortened and the reduction of the turnaround time can be realized. Further, since the operations in the initial process state are those executed only once after the powering on of the apparatus, improvement of operational efficiency and saving of consumable articles in inspection facilities such as hospitals, laboratories, inspection centers, etc. can be expected. Furthermore, by automating the powering on of the apparatus by using a timer, etc. for example, the above operations can previously be executed before the operator arrives at the inspection facility, from which further improvement of the operational efficiency can be expected. Among the four preparatory operations, the "reaction vessel discarding operation" and the "pre-cleaning liquid replacement operation" are executed in parallel with the sample measurement in the operation state. First, the reason why the "reaction vessel discarding operation" can be executed in parallel with the sample measurement will be explained below with reference to FIG. 3.

In conventional techniques, the check on the presence/absence of the remaining used reaction vessel and the discarding of the remaining reaction vessel are conducted for all the positions on the reaction vessel setting mechanism in the preparation process. In the sample measurement in the operation state, however, the reaction vessels are used for their respective inspection items in order of the positions numbers marked on the reaction vessel setting mechanism. Thus, not all the positions are necessarily required to be vacant as long as positions necessary for the inspections are open. For example, assuming that the reaction vessel to be used for the inspection of the first sample after the start of the operation is one having the position number 1, the check on the presence/absence of the used reaction vessel and the discarding of the remaining reaction vessel in the preparatory operations are carried out for the position 1 only. Since the second and subsequent positions are only required to be open just before their respective reaction vessels are used, the check on the presence/absence of the used reaction vessel and the discarding process are continued also after the apparatus has shifted to the operation state.

Next, the reason why the "pre-cleaning liquid replacement operation" can be conducted in parallel with the sample measurement will be explained below with reference to FIG. 5B (5-2).

In the sample measurement during the operation of the apparatus, the pre-cleaning operation does not necessarily have to be executed in the preparation process as long as the pre-cleaning is finished before the final stage of the measurement (i.e., immediately before the signal detection). Therefore, the pre-cleaning operation may also be executed after the apparatus has shifted to the operation state.

As described above, in an example according to the present invention, among the preparatory operations which are executed in the preparation process in the conventional techniques, the "system liquid replacement operation" and the "sample nozzle pressure sensor checking operation" are executed in the initial process just after the power of the apparatus is turned on and the "reaction vessel discarding operation" and the "pre-cleaning liquid replacement operation" are executed in the operation state in parallel with the sample measurement. As a result, the required time t2 of the preparation process can be reduced as shown in FIG. 5B (5-2) compared to the required time t1 in the conventional technique.

Figure 6:
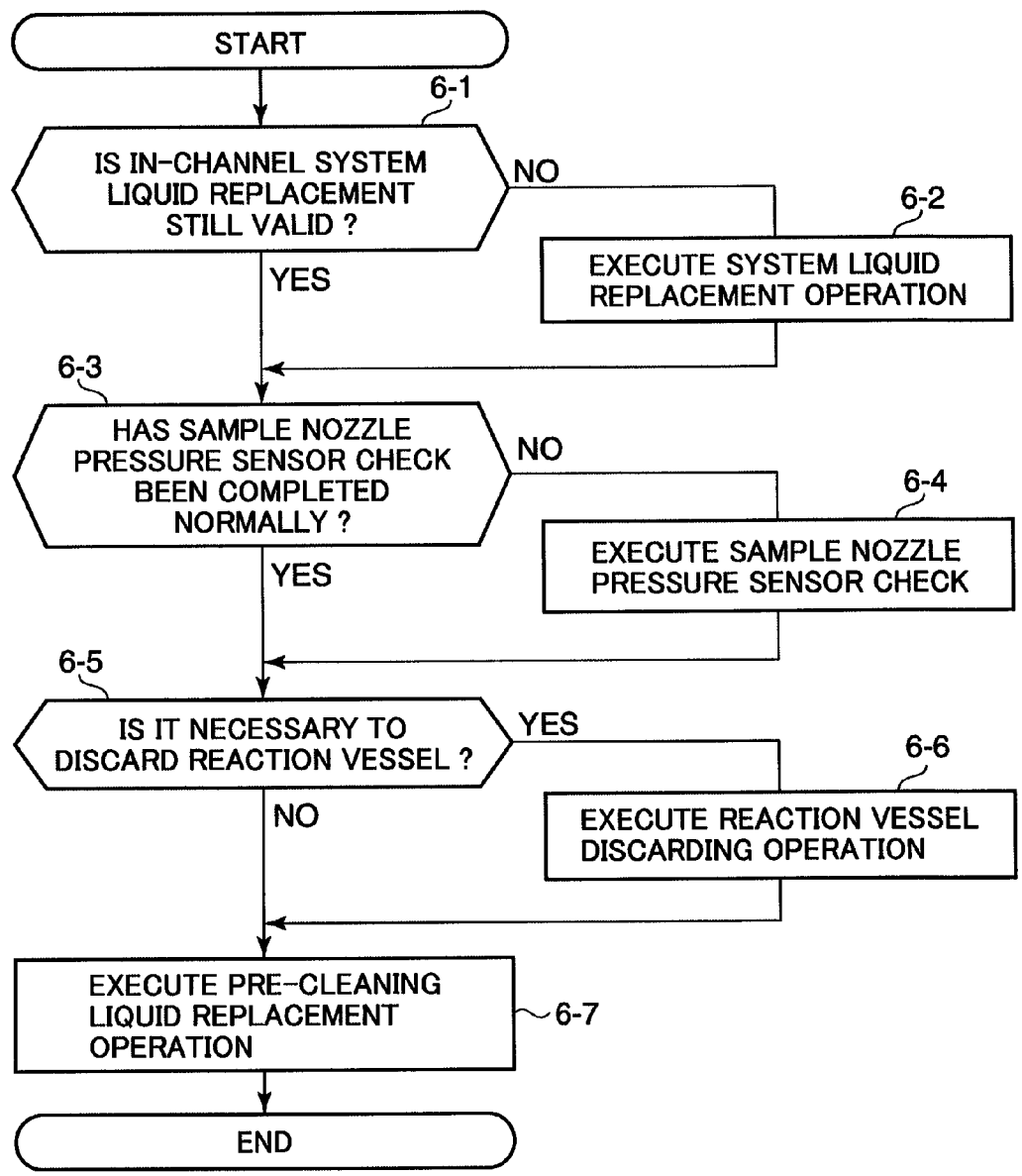
FIG. 6 is a flow chart showing logic for optimizing the analysis preparation process.

In the present invention, the apparatus automatically judges whether the four preparatory operations have to be executed or not based on the operational conditions of the user's inspection facility and sets logic for carrying out an optimum and shortest preparation process under the current conditions. FIG. 6 shows a flow chart for the apparatus for automatically judging/executing the optimum and shortest preparation process based on the conditions. At the start of the preparation process, the apparatus checks whether the in-channel system liquid replacement is still valid or not (step 6-1). If valid, the process advances to step 6-3. If not valid, the process advances to step 6-2. In the step 6-2, the apparatus executes the system liquid replacement operation and thereafter advances to the step 6-3. In the step 6-3, the apparatus checks whether the sample nozzle pressure sensor check has been completed normally or not. If the check has been completed normally, the process advances to step 6-5, otherwise the process advances to step 6-4. In the step 6-4, the apparatus executes the sample nozzle pressure sensor check and thereafter advances to the step 6-5. In the step 6-5, the apparatus checks whether the discarding of the reaction vessel is necessary or not. If unnecessary, the process advances to step 6-7. If necessary, the process advances to step 6-6. In the step 6-6, the apparatus executes the reaction vessel discarding operation and thereafter advances to the step 6-7. In the step 6-7, the apparatus executes the pre-cleaning liquid replacement operation and ends the process. By the above logic, the analysis preparation process is optimized.

Figure 7:
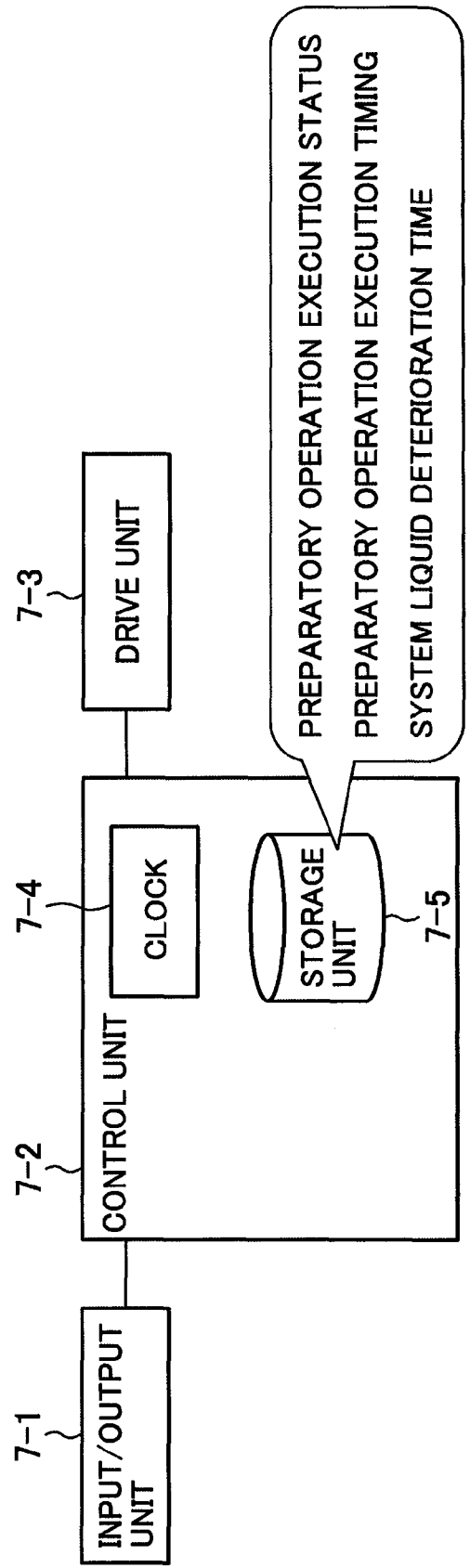
FIG. 7 is a block diagram showing an example of a system configuration in accordance with the embodiment.

Next, an example of the apparatus configuration implemented by the present invention will be explained referring to FIG. 7. The apparatus comprises at least an input/output unit 7-1, a control unit 7-2 and a drive unit 7-3. The control unit 7-2 includes a clock 7-4 and a storage device 7-5. Data regarding "preparatory operation execution status", "preparatory operation execution timing", "system liquid deterioration time", etc. are stored in the storage device.

Next, means will be explained below for keeping the freshness of the system liquid even when the system liquid replacement operation is executed in the initial process just after the powering on of the apparatus according to the present invention. The purpose of the system liquid replacement operation is to previously replace the system liquid inside the channel with new system liquid so as to supply the new system liquid to the detecting device in the immunological analyzing apparatus. However, if the time period before the start of the measurement (i.e., the standby time shown in FIG. 5B (5-2)) is long in the case where the system liquid replacement operation is executed in the initial process just after the powering on of the apparatus, the system liquid can deteriorate in the period.

Figure 8:
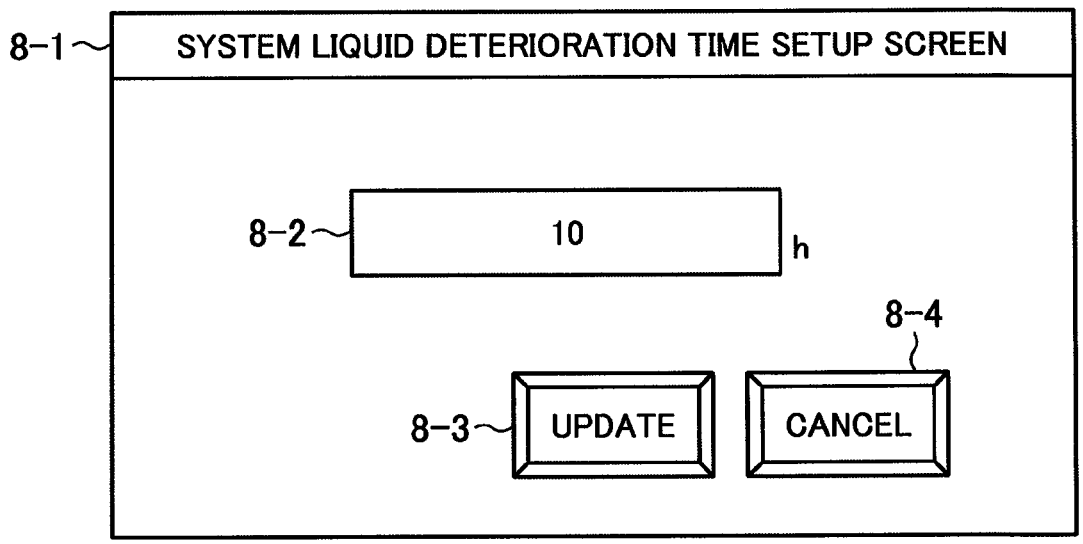
FIG. 8 is a schematic diagram showing an example of an operation screen which is used for setting a time in which the system liquid is supposed to deteriorate.

Further, since the standby state is a state in which the maintenance of the apparatus can be done, there are cases where no system liquid exists in the channel when an operator or service person has performed a maintenance operation of replacing the system liquid in the channel with water. To prevent such situations, the apparatus is equipped with means which automatically reexecutes the system liquid replacement operation in the preparation process at the start of the measurement only when the standby state has continued longer than a prescribed time period or a maintenance operation like the water replacement has been performed. FIG. 8 shows a system liquid deterioration time setup screen which is displayed on the operation screen of the immunological analyzing apparatus.

The reference numeral 8-1 represents the system liquid deterioration time setup screen for setting the system liquid deterioration time, 8-2 represents an input area for inputting the system liquid deterioration time, 8-3 represents an update button, and 8-4 represents a cancel button. The user can arbitrarily set a deterioration time corresponding to the system liquid used in the inspection facility in the input area 8-2. When the user presses the update button 8-3 after setting the deterioration time, the setting is stored in the storage device of the apparatus. When the user presses the cancel button 8-4, the apparatus returns to the previous screen with no further operation.

Figure 9:
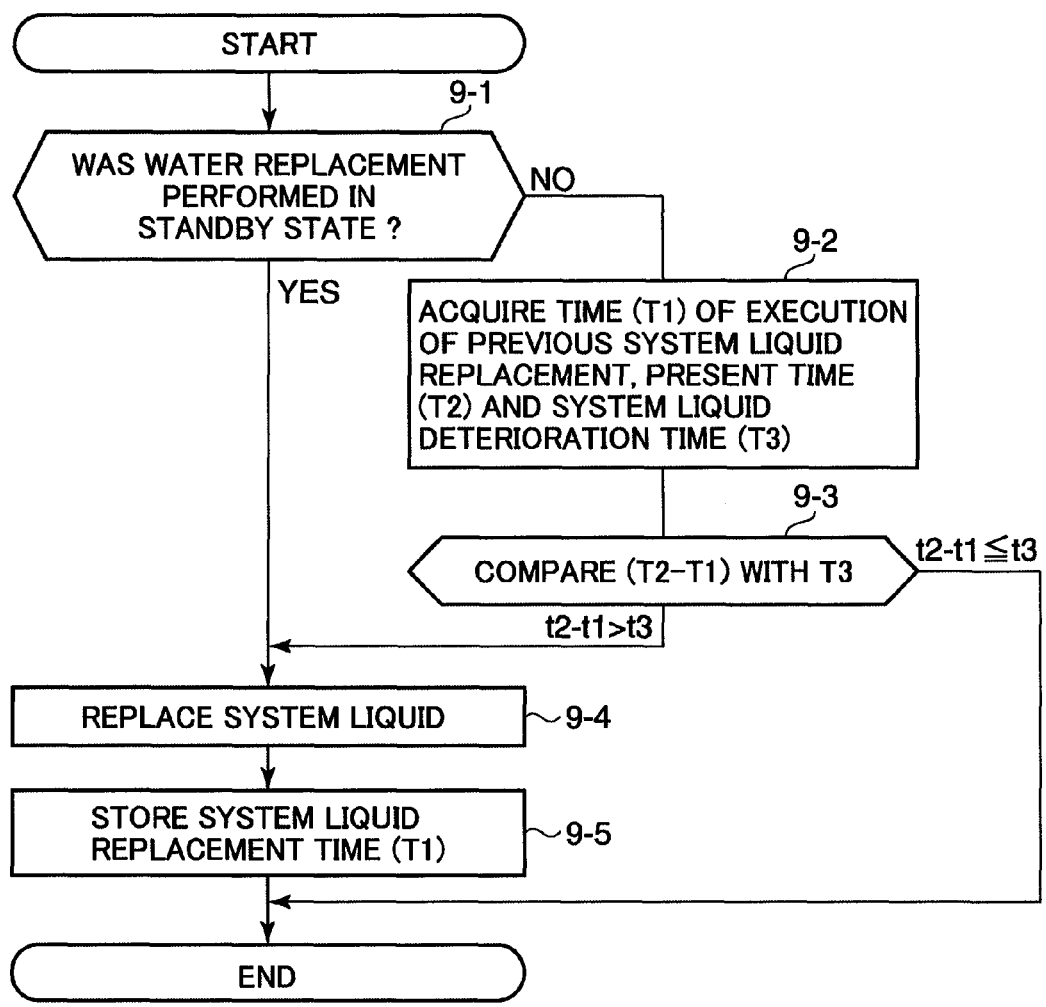
FIG. 9 is a flow chart showing logic for the apparatus for judging whether the system liquid is valid or invalid, executing the system liquid replacement operation if the system liquid is invalid, and skipping the system liquid replacement operation if the system liquid is valid.

FIG. 9 is a flow chart showing logic for automatically executing the system liquid replacement operation in the preparation process at the start of the measurement only when the standby state has continued longer than a prescribed time period or a maintenance operation like the water replacement has been performed. The flow chart corresponds to the details of the step 6-1 in FIG. 6. At the start of the preparation process, the apparatus checks whether the water replacement has been performed or not (step 9-1). If the water replacement has been performed, the process advances to step 9-4, otherwise the process advances to step 9-2. In the step 9-2, the apparatus acquires the time of execution of the previous system liquid replacement operation, the present time and the system liquid deterioration time which has been set on the screen shown in FIG. 8, and each of time is assumed to be t1, t2 and t3. In the next step 9-3, the apparatus compares t2−t1 with t3. If t2−t1≤t3, the process is ended. If t2−t1>t3, the process advances to the step 9-4. In the step 9-4, the apparatus executes the system liquid replacement operation. In the next step 9-5, the apparatus stores the time of execution of the system liquid replacement operation. The logic explained above makes it possible to execute the system liquid replacement operation in the preparation process at the start of the measurement only in cases where the standby state has continued longer than a prescribed time period or a maintenance operation like the water replacement has been performed, while skipping the system liquid replacement operation in the preparation process in the other cases.

Figure 10A:
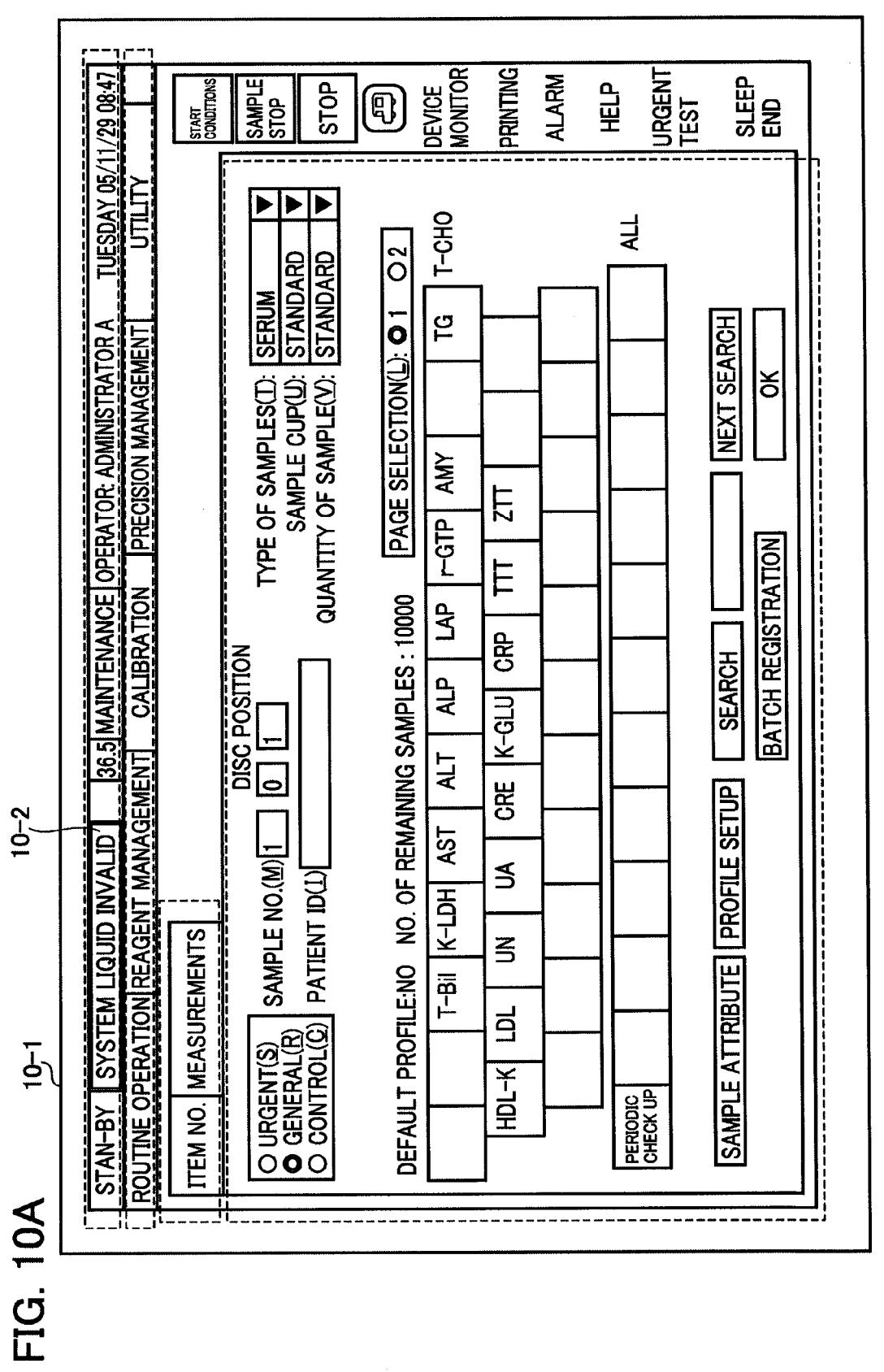
Figure 10B:
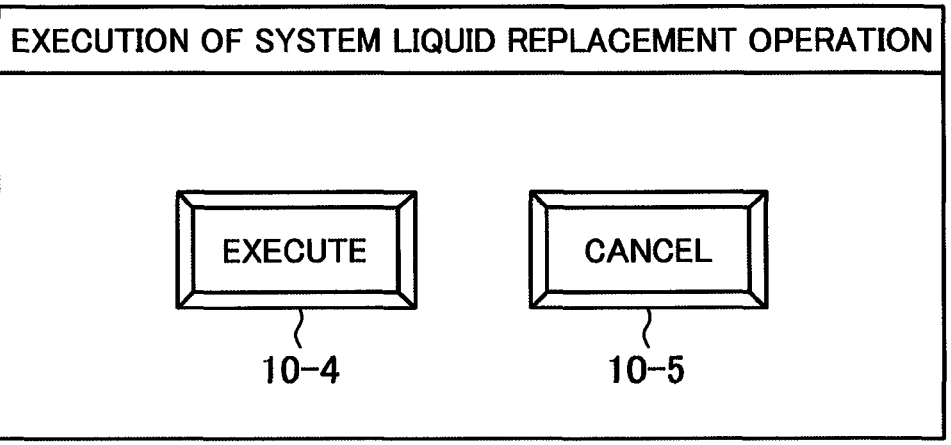
FIG. 10B is a schematic diagram showing an example of an operation screen for executing the system liquid replacement operation and validating the system liquid when the system liquid is invalid on the screen for notifying the user whether the system liquid is valid or invalid.

It is also possible to equip the apparatus with means which notifies the user of the invalidity of the system liquid when the system liquid currently inside the channel is invalid such as when the standby state has continued longer than a prescribed time period or a maintenance operation like the water replacement has been performed and lets the user validate the system liquid at an arbitrary time during the standby. FIGS. 10A and 10B show an example of such means. FIG. 10A (10-1) shows an example of the operation screen of the immunological analyzing apparatus. For example, an area/button 10-2 for displaying the validity/invalidity of the system liquid is arranged at an arbitrary position on the operation screen. The area/button 10-2 indicates whether the system liquid currently in the channel is valid or invalid. When the user presses the button when the system liquid is invalid, the apparatus displays a system liquid replacement operation execution window 10-3 shown in FIG. 10B. The reference numeral 10-4 represents an execution button. When the execution button 10-4 is pressed, the apparatus executes the system liquid replacement operation and thereby validates the system liquid currently in the channel. The reference numeral 10-5 represents a cancel button. When the cancel button 10-5 is pressed, the apparatus returns to the previous screen with no further operation. With this means, even when the system liquid is invalid, the user can validate the system liquid at an arbitrary time during the standby. Consequently, the time necessary for the preparation process can be reduced.

There are cases, depending on the user, where the apparatus is operated in a style in which a certain long time period exists between the startup of the apparatus and the start of the measurement. In such cases, a larger amount of system liquid is consumed in the technique 5-2 which shortens the turnaround time of the first measurement after the start compared to the conventional technique 5-1. To deal with this problem, the apparatus is equipped with means for letting the user set the timing of execution of the preparatory operations based on the user's style of operation.

The reference numeral 11-1 represents a preparatory operation execution timing setup screen, 11-2 represents the names of the preparatory operations, 11-3 represents pull-down menus for the selection of the execution timings, 11-4 represents an update button, and 11-5 represents a cancel button. The user sets the timings of the operations using the pull-down menus. When the update button 11-4 is pressed, the current settings are stored in the storage device of the apparatus and subsequent preparatory operations are executed with the timings according to the settings on the screen. When the cancel button 11-5 is pressed, the apparatus returns to the previous screen with no further operation.

DESCRIPTION OF REFERENCE NUMERALS 1-1 state before execution of the system liquid replacement operation
1-2 system liquid bottle
1-3 channel for system liquid
1-4, 2-4, 4-4 syringe
1-5, 4-5 first valve
1-6, 4-6 second valve
1-7, 4-7 third valve
1-8 reservoir separately provided in the apparatus for supplying the system liquid to the detecting device
1-9 drain hole for dumping unnecessary liquid into the drain
1-10 state in which old system liquid in the channel has been replaced with fresh system liquid
2-1 sample suction hole
2-2 channel
2-3 pressure sensor for checking whether there is a clog in the channel
2-5 valve
2-6, 4-14 internal washing water supply hole
3-1 rotary reaction vessel setting mechanism
3-2 disposable reaction vessel
3-3 position number on the reaction vessel setting mechanism
3-4 reaction vessel transfer mechanism
3-5 holding mechanism of the reaction vessel transfer mechanism
3-6 waste bag for used reaction vessels
4-1 state before execution of the pre-cleaning liquid replacement operation
4-2 pre-cleaning liquid bottle
4-3 channel for pre-cleaning liquid
4-8 fourth valve
4-9 fifth valve
4-10 discharge nozzle
4-11 suction nozzle
4-12 reservoir for supplying the pre-cleaning liquid to the pre-cleaning device
4-13 drain hole for dumping unnecessary liquid into the drain
4-15 state in which old pre-cleaning liquid in the channel has been replaced with fresh pre-cleaning liquid
5-1 schematic diagram showing the process flow from the powering on of the apparatus to the outputting of the result in the conventional technique
5-2 schematic diagram showing the shortening of the preparation process achieved by employing the present invention
7-1 input/output unit
7-2 control unit
7-3 drive unit
7-4 clock
7-5 storage device
8-1 system liquid deterioration time setup screen
8-2 input area for inputting system liquid deterioration time
8-3, 11-4 update button
8-4, 10-5, 11-5 cancel button
10-1 example of the operation screen of the immunological analyzing apparatus
10-2 area/button for displaying the validity/invalidity of the system liquid
10-3 system liquid replacement operation execution window
10-4 execution button
11-1 preparatory operation execution timing setup screen
11-2 preparatory operation name
11-3 pull-down menu for selection of execution timing

The invention claimed is:

1. A method for preparing an automatic analyzer for analysis of a sample, the automatic analyzer having a detector as an analysis device and a control unit configured to control the detector and a sample analysis operation in connection therewith, the method comprising:

displaying, on a display unit, based on instructions received from the control unit, a selection screen enabling, for a preparatory operation of a plurality of preparatory operations, selection of one of performing the preparatory operation in an initial process after powering on the automatic analyzer and performing the preparatory operation in parallel with a sample analysis operation;

receiving, by the control unit, a selection of performing the preparatory operation in the initial process after powering on the automatic analyzer or in parallel with the sample analysis operation after the suction of the sample;

when the selection of performing the preparatory operation in the initial process after powering on the automatic analyzer has been received, controlling, by the control unit, the automatic analyzer to perform the preparatory operation during the initial process after powering on the automatic analyzer; and when the selection of performing the preparatory operation in parallel with the sample analysis operation and when a measurement start instruction to start the sample analysis operation have been received, controlling, by the control unit, the automatic analyzer to perform the preparatory operation in parallel with the sample analysis operation after suctioning of the sample.

2. The method according to claim 1, wherein the preparatory operations include at least one operation selected from the group consisting of:

a system liquid replacement operation replacing liquid to be used in a reaction of the sample to be detected by the detector during analysis, a sample nozzle pressure sensor checking operation, a reaction vessel discarding operation, and a pre-cleaning liquid replacement operation replacing pre-cleaning liquid for a pre-cleaning device.

3. The method according to claim 2, wherein the control unit is programmed to automatically execute the system liquid replacement operation at the start of the measurement in cases where the timing of the preparatory operation of the plurality of preparatory operations has been selected to be in the initial process after the powering on of the analyzer and an elapsed time since the latest system liquid replacement to the start of the measurement has exceeded a preset time period.

4. The method according to claim 2, wherein the control unit is programmed to automatically execute the system liquid replacement operation at the start of the measurement in cases where the timing of the preparatory operation of the plurality of preparatory operations has been selected to be in the initial process after the powering on of the analyzer and the system liquid in a channel of the automatic analyzer has been lost before the start of the measurement due to execution of an apparatus maintenance operation such as water replacement in the channel.

5. The method according to claim 3, further comprising the step of:

displaying, on the display unit, based on instructions received from the control unit, an indication of whether the elapsed time since the latest system liquid replacement to the start of the measurement has exceeded the preset time period.

6. A method for preparing an automatic analyzer for analysis, the automatic analyzer having a detector as an analysis device, the method comprising:

displaying, on a display unit, based on instructions received from the control unit, a selection screen including a region that corresponds to a preparatory operation of a plurality of operations, where the region enables selection of at least one of performing the preparatory operation in an initial process and performing the preparatory operation in parallel with sample analysis operations;

receiving, by the control unit, a selection of performing the preparatory operation in the initial process or in parallel with the sample analysis operations via the region of the display unit;

storing, by a storage device coupled to the control unit, the selection of performing the preparatory operation in the initial process or in parallel with the sample analysis operations;

after the selection of performing the preparatory operation in the initial process after powering on the automatic analyzer has been stored, controlling, by the control unit, the automatic analyzer to perform the preparatory operation in the initial process after the automatic analyzer is powered on and before suctioning of a sample; and after the selection of performing the preparatory operation in parallel with the sample analysis operations has been stored and after a measurement start instruction has been received by the control unit, controlling, by the control unit, the automatic analyzer to perform performing the preparatory operation in parallel with the sample analysis operations after suctioning of the sample.

* * * * *